United States Patent [19]

Morr et al.

[11] Patent Number: 5,124,106
[45] Date of Patent: Jun. 23, 1992

[54] METHOD OF MAKING A FEMORAL RASP

[75] Inventors: James J. Morr, Leesburg; William F. Long, Jr., Warsaw; John F. Niccum, Akron, all of Ind.

[73] Assignee: Zimmer, Inc., Warsaw, Ind.

[21] Appl. No.: 676,776

[22] Filed: Mar. 25, 1991

[51] Int. Cl.⁵ ............................................. B29C 33/40
[52] U.S. Cl. .................................. 264/221; 264/222; 264/225; 264/277; 264/278; 264/317; 606/85
[58] Field of Search ....................... 606/85; 623/18, 23; 264/222, 275, 277, 278, DIG. 30, 221, 317, 261, 225

[56] References Cited

U.S. PATENT DOCUMENTS

| | | | |
|---|---|---|---|
| D. 273,806 | 5/1984 | Bolesky et al. | 606/85 |
| 3,608,051 | 9/1971 | Scott | 264/261 |
| 3,874,003 | 4/1975 | Moser et al. | 606/85 |
| 4,108,955 | 8/1978 | Thom | 264/261 |
| 4,335,428 | 10/1982 | Deloison et al. | 623/18 |
| 4,454,612 | 6/1984 | McDaniel et al. | 623/18 |
| 4,552,136 | 11/1985 | Kenna | 606/85 |
| 4,612,160 | 9/1986 | Donlevy et al. | 419/2 |
| 4,778,469 | 10/1988 | Lin et al. | 264/221 |
| 4,942,653 | 7/1990 | Hawkinson | 264/277 |

FOREIGN PATENT DOCUMENTS 0012146 6/1980 European Pat. Off. ............ 623/18

Primary Examiner—Jay H. Woo
Assistant Examiner—Robert B. Davis
Attorney, Agent, or Firm—Todd A. Dawson

[57] ABSTRACT

A method of making a femoral rasp wherein the hip stem implant is used to make a two part mold. The mold halves are separated and the implant removed to yield left and right mold halves representing corresponding halves of the hip stem. The cavities of the mold halves are lined with wax and a plurality of blades are imbedded into the wax such that an anchor portion of each of the blades remains exposed. The mold halves are connected together and a stem of handle is inserted therein. A moldable material such as PMMA is poured into the mold and allowed to cure. When the PMMA is hard or cured, the mold halves are separated and the wax is removed from the rasp body exposing the cutting surfaces of the teeth.

3 Claims, 3 Drawing Sheets

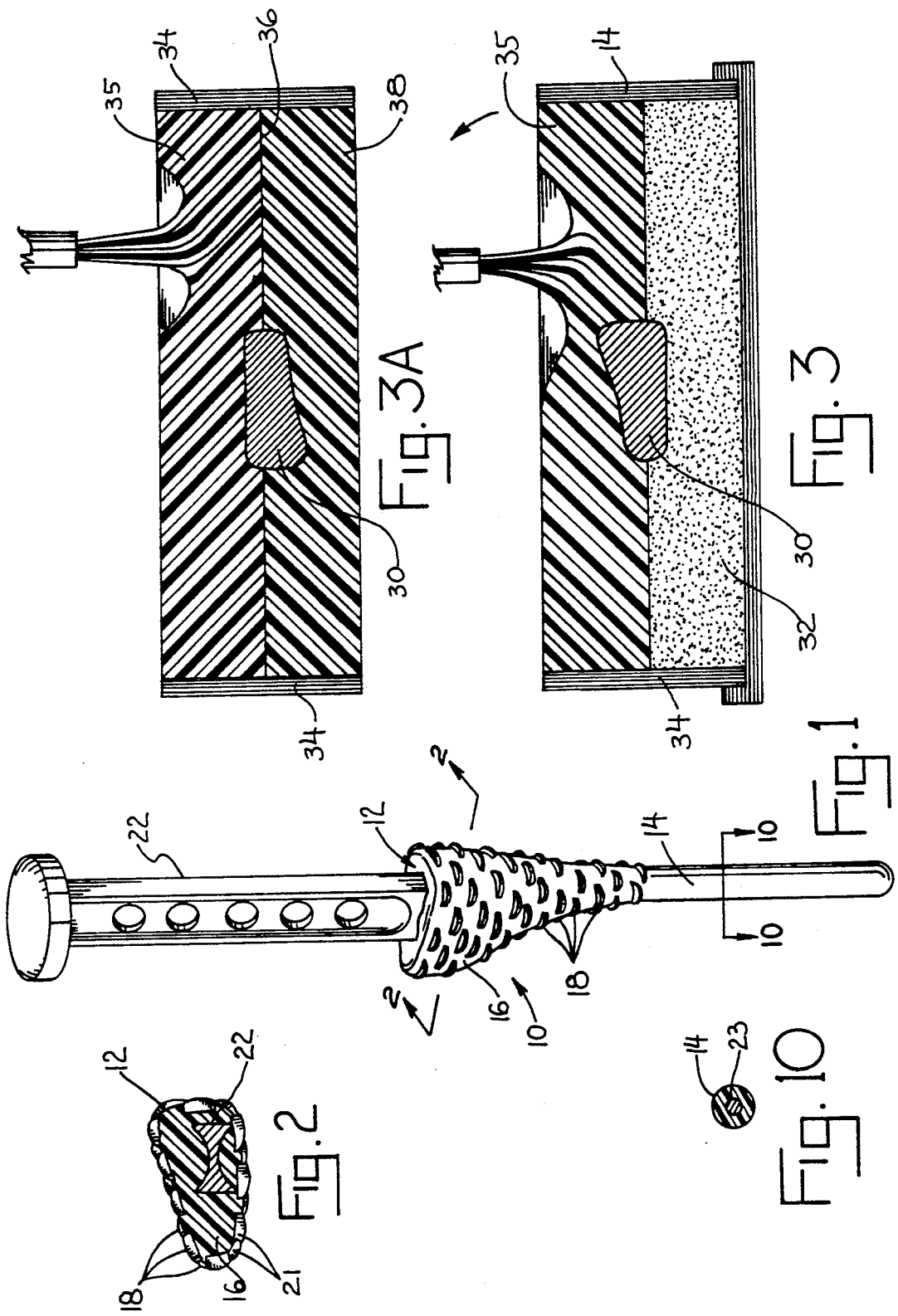

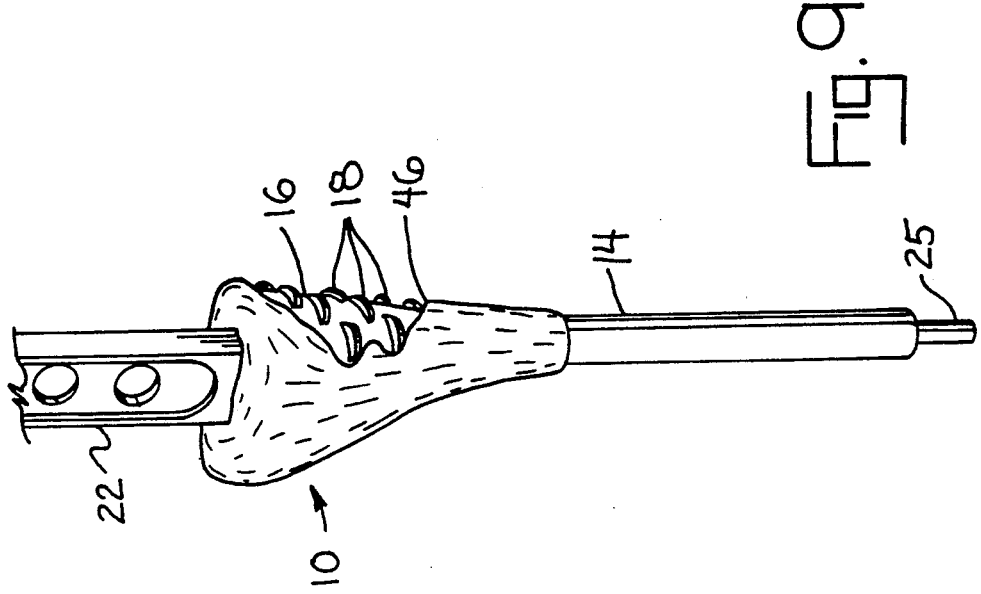
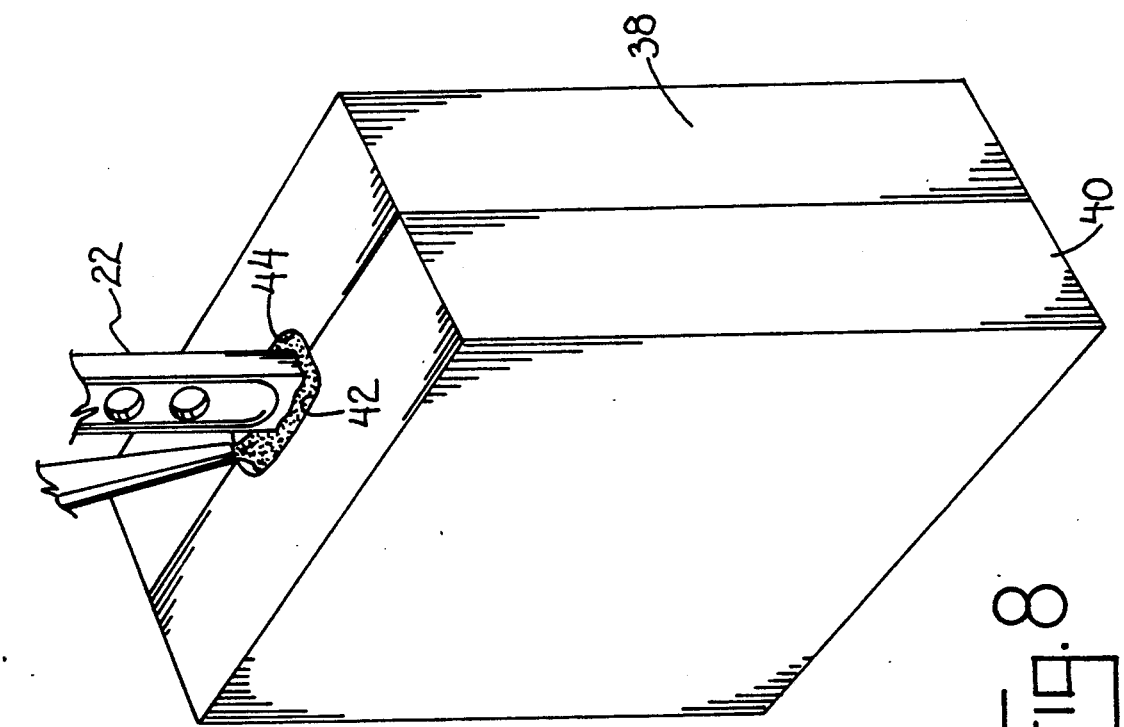

5,124,106

METHOD OF MAKING A FEMORAL RASP

FIELD OF THE INVENTION

This invention relates to femoral rasp and the method of manufacturing the rasp but more importantly has special relevance to a femoral rasp for an uncommonly sized hip stem implant and the method of making the uncommonly sized rasp.

BACKGROUND OF THE INVENTION

Generally, hip stem implants come in a variety of common shapes and sizes to accommodate the vast majority of patients requiring a hip stem replacement. To ensure a proper seating of the hip stem a like variety of shaped and sized rasps are provided to properly form the proximal medullary canal of the femur. Therefore, for each size and shape of prosthetic hip stem implant there is generally a correspondingly sized and shaped rasp. Typically a hospital would have on hand a complete set of commonly sized and shaped rasps. After one of the common rasps is used, it is cleaned and sterilized for use over and over again.

A problem is experienced when, for reasons not detailed here, a prosthetic hip stem implant is required which is of an uncommon shape or size. In such circumstances, the manufacturer is called upon to create a "one of a kind" implant for the patient. This may be accomplished in a number of valid methods but perhaps is more commonly accomplished through computer aided design and computer numerical controlled milling machines. This known process is able to accurately and economically produce the off sized or irregularly shaped implant as required. As mentioned, it is common for a corresponding rasp to be provided for a particular size of implant. Therefore, the rasp provided for the one of kind implant is itself "one-of-a-kind" in size and shape.

Heretofore, the one-of-a-kind rasps for the one-of-a-kind implant are formed from the same material as the reusable more commonly sized rasps. To manufacture the one-of-a-kind rasp a significant amount of skilled labor is required to machine and cut the rasp teeth in its outer surface. Such a process is labor intensive and thereby costly to a manufacturer. While it is true the rasp may be formed on a CNC machine consistent with the industry practice regarding common size rasps, such is considered expensive and equally labor intensive in terms of re-tooling time, down time for re-tooling, lost machine productivity and engineering time. Therefore, the hand grinding approach to producing the one-of-a-kind rasp is considered to be the least burdensome of the two methods. The cost of the special rasp is especially burdensome when it is considered that the rasp is not for reuse and should be discarded after surgery since it is unlikely that the exact one-of-a-kind implant corresponding to the rasp would ever be called for again.

Therefore, for each special implant sold by a manufacturer a special rasp is required which is discarded after use. Finally, manufacturing the rasp in the manner described above is a time consuming process and requires additional lead time before delivery to the surgeon.

SUMMARY OF THE INVENTION

This invention eliminates the problems discussed above by providing an economical femoral rasp manufactured by an economical and time efficient method. The method includes using the implant, or a plastic replica commonly made as a proof of the implant, as a positive to form the interior cavity for a two part mold. The mold cavity, when the mold halves are assembled together, is an exact negative copy of the size and shape of the stem portion of the implant. The mold is separated into its two halves and each cavity is lined with a thin layer of mineral wax or other type of wax used in lost wax casting. A plurality of blades or teeth are pressed into the wax until the outer cutting surface of the blades contact the mold material and a base portions extends internally into the cavity. The mold is made from a material hard enough so that the blades will not dig into the surface. The two mold halves are assembled in a known manner and a handle member is inserted in to the end of the mold and supported therein in a common manner. A moldable liquid which hardens when cured such as poly methyl methacrylate (PMMA) is poured into the mold about the handle member and allowed to cure. When fully cured, the mold halves are separated. The wax is then removed from the rasp body to expose the cutting surfaces of the blades. The main body portion or anchor portion of each of the blades is molded into the rasp body. Since the blades do not penetrate into the mold material, the periphery formed by the outer cutting surfaces of the blades exactly coincided with the outer periphery of the hip stem implant. The moldable liquid may be PMMA or any suitable material having a sufficient strength when cured to hold the blades during use of the rasp and having a viscosity such that when poured will completely fill the mold cavity without voids adjacent the blades.

The rasp formed by the method of this invention may be produced economically and generally faster than the special sized rasps currently known.

Accordingly, it is an object of this invention to provide for a novel rasp and method of making the same.

Another object of the invention is to provide an economical method of making a one-of-a-kind rasp.

Another object of the invention is to provide an economical one-of-a-kind femoral rasp.

Other objects of the invention will become apparent upon a reading of the following description taken with the accompanying drawings.

BRIEF DESCRIPTION OF THE DRAWINGS

FIG. 1 is a perspective view of the femoral rasp of the invention formed by the method of this invention.

FIG. 2 is a sectional view taken from line 2—2 of FIG. 1.

FIGS. 3, 3A, and 4-9 illustrate the manufacturing steps required in the
this invention to form the rasp of FIG. 1.

FIG. 10 is a cross-sectional view taken along line 10-10 of FIG. 1.

DESCRIPTION OF THE PREFERRED EMBODIMENT

Figure 6:
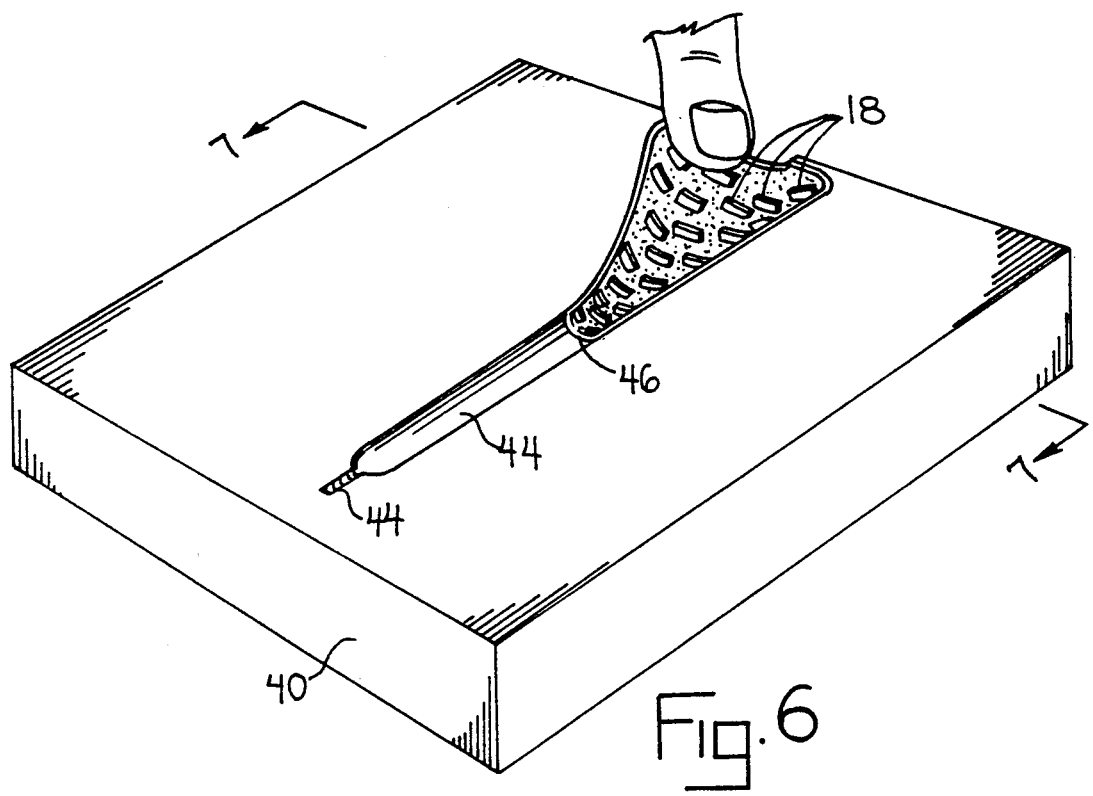
Figure 4:
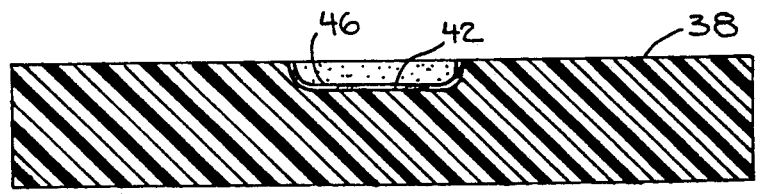
Figure 5:
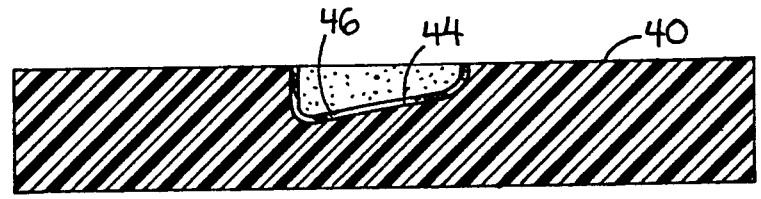

The preferred method and embodiment herein disclosed are not intended to be exhaustive or to limit the application to the precise method or form disclosed. Rather, it is chosen and described so that others skilled in the art might utilize its teachings.

As is illustrated in the figures, rasp 10 includes a body 12 preferably formed from poly methyl methacrylate (PMMA) and having a lower stem 14 and a widened neck 16. A plurality of blades 18 are molded into the neck portion 16 of rasp 10 to extend outwardly as shown. A handle 22 extends longitudinally from the proximal portion of the rasp. Handle 22 includes a rod 23 which extends into stem 14 of rasp body 12. It should be understood that each blade 18 includes an anchor portion 21 which extends into body 12 for support and cutting portion 20 extending outwardly from the body. In the preferred embodiment blades 18 are formed from metal and are oriented such that their cutting portions 20 perform a scraping action when the rasp is driven into the medullary canal of the femur. The specific location of the blades along body 12 may be considered generally random in nature.

In use, the surgeon prepares the medullary canal in a known manner and inserts the stem 14 of rasp 10 into the canal (not shown). By striking the end of the handle, rasp 10 is driven into the canal such that a quantity of bone stock is removed by each blade contacting the femur. The rasp is removed to allow the bone particles to fall from the rasp. Again the rasp is driven into the canal and additional bone stock is removed by the blades. Repeated insertion and removal of the rasp enlarges the canal until the entire neck 16 of the rasp is accommodated by the canal or until a time when the surgeon believes sufficient bone stock has been removed for a proper seating of the special sized implant. This method of enlarging the canal for accommodation of the implant is well known and is explained briefly here merely for illustration of the intended use of the rasp.

The steps involved in the method of forming rasp 10 described above are illustrated in FIGS. 3-9. To form rasp 10 the actual implant 30, or the plastic model thereof, is imbedded into a clay mass 32 such that only one half including a side wall and portions of the medial wall and lateral wall of implant 30 are exposed. A frame 34 is placed around the clay mass to extend above the surface of the clay. The exposed surface of the implant is covered with a release agent to prevent the implant from sticking to the mold compound. A mold compound 35 is poured over the implant to fill frame 34 and allowed to harden. The frame and clay are removed and the newly formed mold half 38 with implant imbedded therein is turned over and the frame built about the newly exposed portion of implant 30. A thin barrier material 36 is placed on the upper surface of the mold half 38 and a release agent is applied to the exposed portion of the implant. Mold compound 35 is poured to cover the implant and fill the frame. When mold compound 35 hardens, the newly formed mold halves 38 and 40 are separated and the implant is removed yielding a cavity 42 in mold half 38 and a cavity 44 in mold half 40. A longitudinal groove 43 is formed into each mold half (only one shown) extending from the distal tip of the mold cavity as illustrated in FIG. 6.

Figure 7:
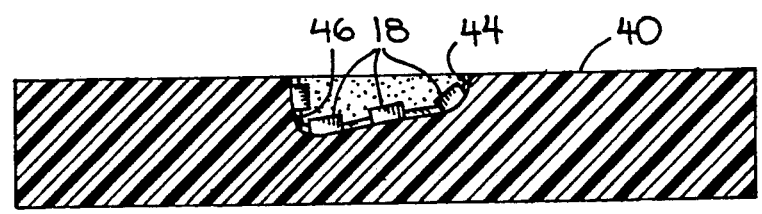

A layer or sheet of wax 46 is pressed into the widened neck portion of mold cavities 42, 44. In the preferred embodiment, the sheet wax includes a self adhesive backing to assist in its adherence to the mold cavity. Next a plurality of teeth 18 are pressed into the wax of each cavity such that the cutting portions 20 of teeth 18 contact the wall of the mold cavities 42, 44 (only cavity 44 is shown in FIGS. 6 and 7). The thickness of wax layer 46 pressed into mold cavities 42, 44 determines the amount of exposed blade after molding as will be evident from the description below. In the preferred embodiment, the mold halves are formed from a material having a hardness when cured such that the teeth 18 are unable to bite in to the material as they are pressed into the wax layer. The stem 23 of handle 22 is inserted into the mold cavity in the approximate longitudinal center of the cavity and is seated within a groove 43. The handle end of handle 22 is supported externally of the cavity by brackets or other such supports not shown. The two mold halves 38, 40 are then assembled and secured together in a known manner. A moldable liquid such as PMMA is poured into the mold cavity formed by cavities 42, 44 and allowed to harden. The moldable liquid should have a viscosity such that the liquid freely flows within the mold cavity and around each anchor portion 21 of blades 18 without creating voids. After the liquid cures or hardens mold halves 38, 40 are separated and the molded part is pulled therefrom. The wax layer 46 on the part is melted or otherwise removed from the rasp body to expose the cutting portions of the blades. The distal tip 25 of stem 23 extending from stem 14 of the rasp is cut from rasp 10. The rasp body is then cleaned and prepared in a manner consistent with molding technology to provide a clean part for sterilization.

Since the blades are inserted into each cavity and pressed against but not into the cavity wall, the outer periphery defined by the cutting blades (indicated by broken lines) is the exact dimension and shape of the stem portion of the hip stem implant used to form the mold cavities. Therefore, using the above method, the manufacturer need only machine one part (the implant) and may mold the appropriate size and shape of rasp to exactly match the implant. Molding the rasp body in the manner described above provides a large cost savings and greatly reduces the manufacturing time and lead time required in comparison to current methods for producing a one-of-a-kind rasp.

It should be understood that the teeth used in the method and rasp of the current invention may be shaped in a number of valid configurations. It should be obvious that whatever shape the blades may take an anchor portion needs to be maintained for molding within the body of the rasp.

It should also be understood that while the invention has been describe in use with a pourable PMMA material such should not be considered a limitation on the invention.

Finally, it should be understood that the invention is not to be limited to the precise form or method described above but may be modified within the scope of the appended claims.

We claim:

1. A method of forming a femoral rasp for shaping the proximal end of a medullary canal of a femur to accommodate a prosthetic hip stem implant, said raps having a body, a plurality of teeth extending outwardly therefrom about the periphery of the body, and handle means extending from said rasp body, wherein the outer periphery defined by said plurality of teeth is substantially identical to the outer periphery of a distal stem of said hip stem implant, said method comprising the steps of:
   a. providing a hip stem implant having a proximal portion and a distal portion, said distal portion having an outer periphery;
   b. making a mold of said implant distal portion and dividing said mold into first and second portions along a longitudinal axis of said implant, wherein said first and second portions each include a cavity substantially similar to a longitudinal half of said distal portion of said implant;

c. lining the cavity of each said first and second mold portion with a spacing material;
d. placing a plurality of teeth in each cavity of each of said first and second mold portions such that a cutting surface of each of said teeth contacts a cavity wall;
e. pressing cutting edges of said teeth into said spacing material such that an anchor portion of each of said teeth extend above said spacing material and into a chamber when said mold halves are secured together.
f. securing said first and second mold portions together with said cavities of said first and second mold portions forming a hollow chamber therebetween;
g. inserting a shaft of said handle means into said chamber;
h. pouring a curable liquid into said chamber and about said teeth and said shaft;
i. allowing said curable liquid to cure and solidify and form said rasp;
j. separating said first and second mold portions and pulling said rasp formed therewithin by said solidified liquid from said mold portions.

2. The method of claim 1 further including the step of:

a. removing said spacing material from said rasp to expose said cutting edges of said teeth, such that said cutting edges extend outwardly of said body.

3. A method of forming a rasp for shaping a medullary canal to accommodate a prosthetic implant, said method comprising the steps of:
a. providing first and second mold portions each having a cavity formed thereon, said cavity of said first and second mold portions representing a portion of said implant such that when said mold portions are connected together the cavities align and form a mold of a portion of said implant;
lining said cavities with a spacer material;
c. providing a plurality of blades; each of said blades including a cutting portion and an anchor portion;
d. pressing said plurality of said blades into said spacing material such that said cutting portion of said blades contact a cavity wall and said anchor portion extends above said spacing material;
e. connecting said first and second mold portions together such that said cavities align to form a mold of a portion of said implant;
f. filling said mold with a liquid which hardens when cured to form said rasp;
g. separating said first and second mold portions and removing said rasp formed by said hardened liquid; and
h. removing said spacing material from said rasp to expose said cutting surfaces of said blades.

* * * * *